United States Patent [19]

Hruska

[11] Patent Number: 4,740,160

[45] Date of Patent: Apr. 26, 1988

[54] WELDABLE CROWNS, BRIDGES AND JOINTING IMPLEMENTS OR MEANS

[75] Inventor: Arturo Hruska, Rome, Italy

[73] Assignee: Titanweld B.V., Amsterdam, Netherlands

[21] Appl. No.: 711,099

[22] Filed: Mar. 13, 1985

[30] Foreign Application Priority Data

Jun. 20, 1984 [IT] Italy ................................ 48425 A/84
Jul. 13, 1984 [IT] Italy ................................ 48564 A/84

[51] Int. Cl.⁴ .................................................. A61C 5/08
[52] U.S. Cl. ...................................... 433/219; 433/181; 433/191; 433/206
[58] Field of Search ............... 433/180, 181, 183, 190, 433/191, 193, 208, 218, 219, 206, 207, 208

[56] References Cited

U.S. PATENT DOCUMENTS

| | | | |
|---|---|---|---|
| 1,372,080 | 3/1921 | Masel | 433/180 |
| 2,514,592 | 7/1950 | Ushanoff | 433/208 |
| 2,776,485 | 1/1957 | Stuart | 433/206 |
| 3,052,982 | 9/1962 | Weinstein et al. | 433/206 |
| 3,429,043 | 2/1969 | Andrews et al. | 433/183 |
| 3,430,344 | 3/1969 | Sekendur | 433/219 |
| 3,727,299 | 4/1973 | Hoffmann et al. | 29/472.7 |
| 4,197,643 | 4/1980 | Burstone et al. | 433/20 |
| 4,310,312 | 1/1982 | Keller et al. | 433/204 |
| 4,380,435 | 4/1983 | Raeder et al. | 433/180 |
| 4,412,819 | 11/1983 | Cannon | 433/20 |
| 4,431,418 | 2/1984 | Kienhöfer | 433/206 |
| 4,610,631 | 9/1986 | Beyer et al. | 433/228.1 |
| 4,661,066 | 4/1987 | Linkow et al. | 433/176 |

FOREIGN PATENT DOCUMENTS 3150039  6/1983  Fed. Rep. of Germany .
1306268 11/1961  France ................... 433/191
 352782  4/1961  Switzerland .

Primary Examiner—Gene Mancene
Assistant Examiner—Adriene J. Lepiane
Attorney, Agent, or Firm—John J. Byrne

[57] ABSTRACT

Dental crowns, bridges and jointing implements or tabs for dental prostheses which are capable of being welded in the mouth are disclosed. These structures are preferably comprised of high purity titanium alloy. The dental crowns are formed as a cast or prepressed central cap in the shape of the tooth to be treated. The crown is additionally provided with one or two tabs which correspond to one or both of the linking sides of the crown with an adjacent crown. The titanium jointing tabs are designed for coupling and welding in the mouth and may be used with crowns or bridges of conventional structure such as gold or a gold alloy. Each jointing implement is provided at one end with a shaped element such as a screw to be rigidly coupled to the crown. The jointing implement is also optionally provided with one or more microindentations on the inside lateral surface to facilitate welding in the mouth with the jointing implement or tab of the crown element associated with the adjacent tooth.

11 Claims, 6 Drawing Sheets

FIG. 5A
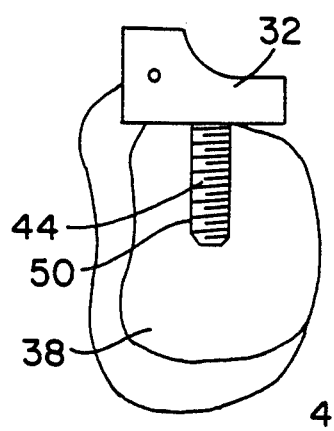
FIG. 5B
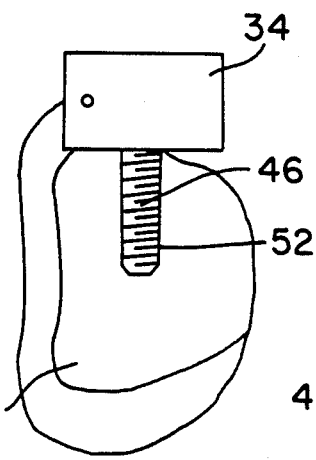
FIG. 5C
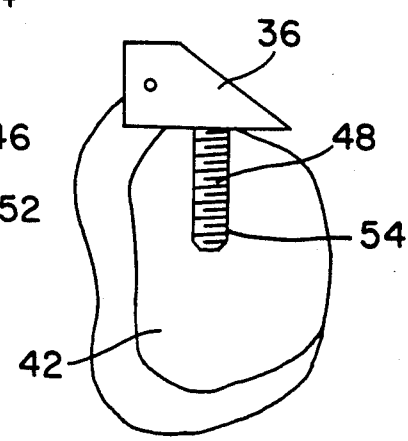
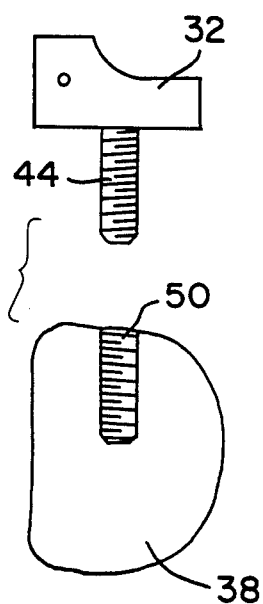
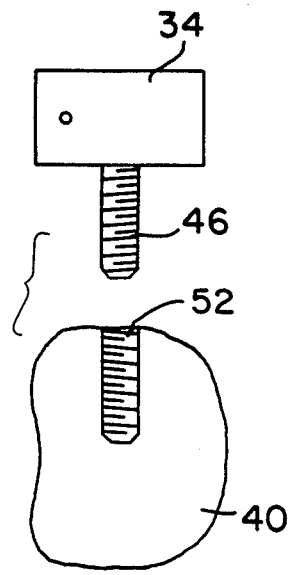
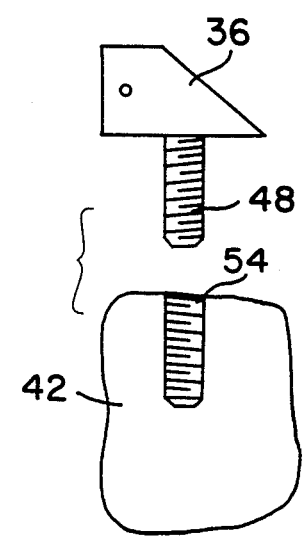
FIG. 6A    FIG. 6B    FIG. 6C

WELDABLE CROWNS, BRIDGES AND JOINTING IMPLEMENTS OR MEANS

FIELD OF THE INVENTION

The present invention relates to dental crowns and bridges, and to jointing implements or means for welding dental prostheses in the mouth.

More particularly, the present invention relates to dental crowns and bridges comprised of high purity titanium metal or alloys having a high concentration of titanium. The crowns and bridges additionally comprise at least one jointing tab which provides a welding surface for connection with a corresponding jointing tab positioned on an adjacent crown or bridge. Each jointing tab may also include one or more microindentations on the inside lateral surface to facilitate the welding operation within the mouth.

In addition, the present invention relates to weldable jointing implements or means which may form the jointing implements or tabs described above or which may also be used in conjunction with other materials which are dentally suitable but which are non-weldable, such as gold and gold alloys, and the like. When used in combination with titanium or other weldable materials, the jointing means and the crown or bridge may be formed as a one-piece unit. When used with non-weldable materials, however, each jointing means is provided at one end with a shaped element such as a screw which is designed for being rigidly coupled to the crown or bridge element. In either instance, the jointing means preferably includes on the inside lateral surfaces one or more microindentations to facilitate an easy welding operation in the mouth with the jointing means of an adjacent crown or bridge.

BACKGROUND OF THE INVENTION

The dental and orthodontic industry has long recognized the need for a careful selection of materials for the construction of crowns, bridges and the like. The dental prostheses must satisfy a number of mechanical requirements such as being able to withstand the stress induced by mastication, hardness, and the like. In addition, the prostheses must possess the necessary biocompatibility characteristics.

For reasons such as those described above, gold and gold alloys such as gold-platinum have been frequently selected for use in the construction of crowns and bridges. However, numerous disadvantages have been occasioned by the use of gold in this manner.

In this connection, the relatively high cost of gold is a significant limiting factor in the utilization of this material in dentistry. Moreover, gold crowns and bridges must be relatively thick to provide necessary strength characteristics, and the often considerable size of such structures limits the thickness of the procelain or plastic aesthetic part of the replacement element (the so-called white surface). Still further, because gold or gold alloys cannot be suitably welded in the mouth, the use of gold in dentistry in the heretofore known prior art is not as flexible in repair and modification as could be obtained using a weldable material wherein individual connections can be broken and reformed.

The problems suggested in the preceding are not intended to be exhaustive, but rather are among many which may tend to reduce the efficiency of prior art dental crowns and bridges. Other problems may also exist; however, those presented above should be sufficient to demonstrate that dental crowns and bridges appearing in the prior art have not been altogether satisfactory.

OBJECTS OF THE INVENTION

It is, therefore, a general object of the present invention to provide dental crowns, bridges and jointing implements or means which will avoid the problems described above.

It is a particular object of the present invention to provide dental crowns, bridges and jointing implements or means comprised of relatively low cost materials.

It is still another object of the present invention to provide dental crowns and bridges which provide for a relatively thick aesthetic outer covering.

It is another object of the present invention to provide dental crowns, bridges and jointing implements or means which are biocompatible.

It is yet another object of the present invention to provide dental crowns, bridges and jointing implements or means which may be relatively thin and provide the required structural strength and hardness.

It is still another object of the present invention to provide dental crowns, bridges and jointing implements or means which may be welded in the mouth.

It is a further object of the present invention to provide dental crowns and bridges in which each tooth replacement element may be individually removed for repair or modification without requiring the removal of the remaining in-place elements.

It is yet a further object of the present invention to provide dental crowns, bridges and jointing implements or means which may be attached to adjacent elements after cementing to reduce or eliminate problems of parallism.

It is still a further object of the present invention to provide jointing implements or means which may be rigidly coupled at one end to elements of suitable dental material and which may be welded at another end to adjacent jointing implements or means in the mouth.

SUMMARY OF THE INVENTION

One embodiment of the present invention intended to accomplish at least some of the foregoing objects comprises a dental crown capable of being welded in the mouth, the dental crown having a central tooth shaped cap portion and at least one jointing tab extending from a side of the central portion, with the jointing tab providing a welding surface thereon.

In another embodiment, the present invention comprises a dental bridge capable of being welded in the mouth, the dental bridge having a plurality of central tooth shaped cap portions wherein at least one jointing tab extends from each of the central cap portions and provides a welding surface thereon.

In another embodiment, the present invention comprises jointing implements or means for welding dental crowns or bridges in the mouth, the jointing means being constructed of weldable material and providing a welding surface thereon, the jointing mean being provided at one end with a coupling portion for attachment to a dental crown or bridge element.

BRIEF DESCRIPTION OF THE DRAWINGS

Other objects and advantages of the present invention will become apparent from the following detailed description of a preferred embodiment of the invention taken in conjunction with the following drawings, wherein:

FIGS. 5A-5C are side views of an alternate construction of the welding surface of the jointing means of the present invention coupled at one end to dental crown by a screw attachment;

FIGS. 6A-6C are side views of the elements of FIGS. 5A-5C prior to attachment;

DETAILED DESCRIPTION

Figure 1:
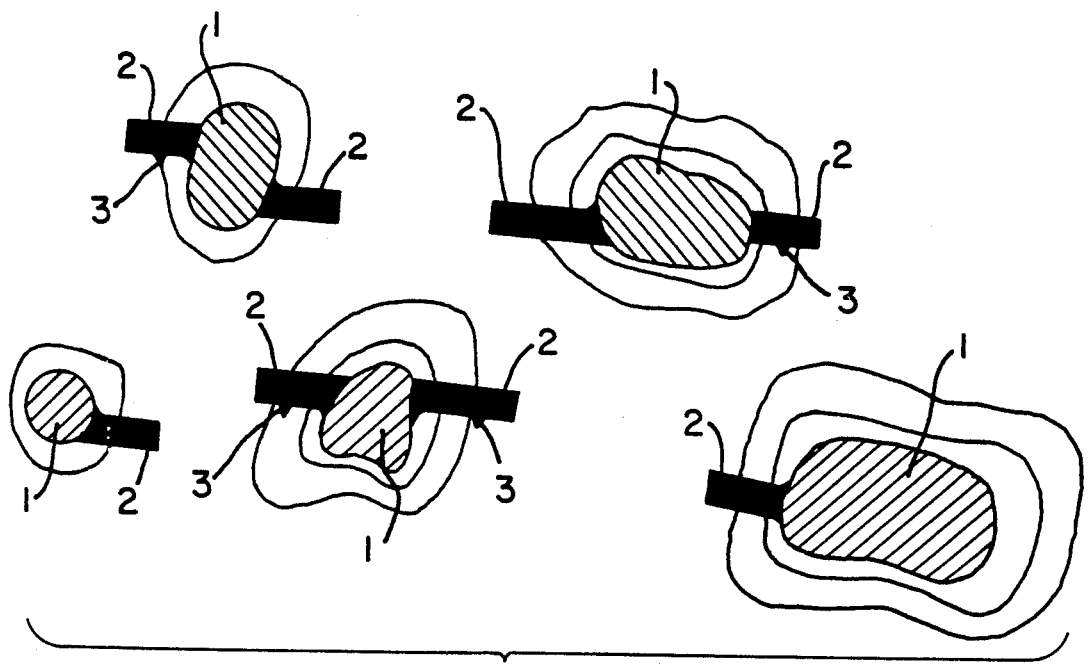
FIG. 1 is a plan view of a plurality of individual crown elements according to this invention.
Figure 2:
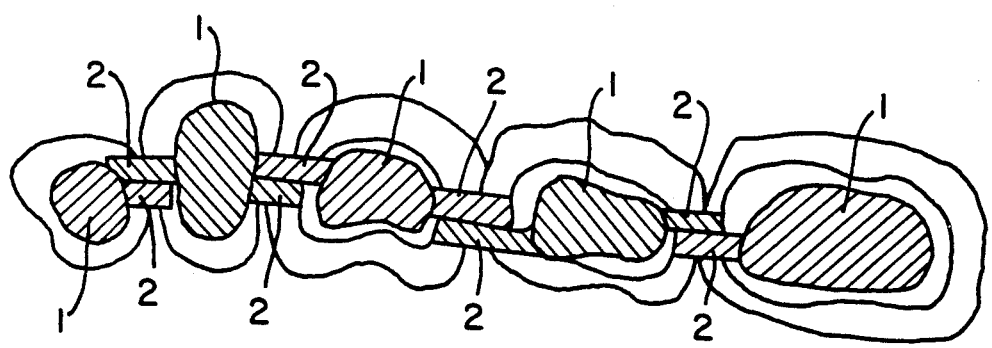
FIG. 2 is a plan view of the elements of FIG. 1 welded together.
Figure 3:
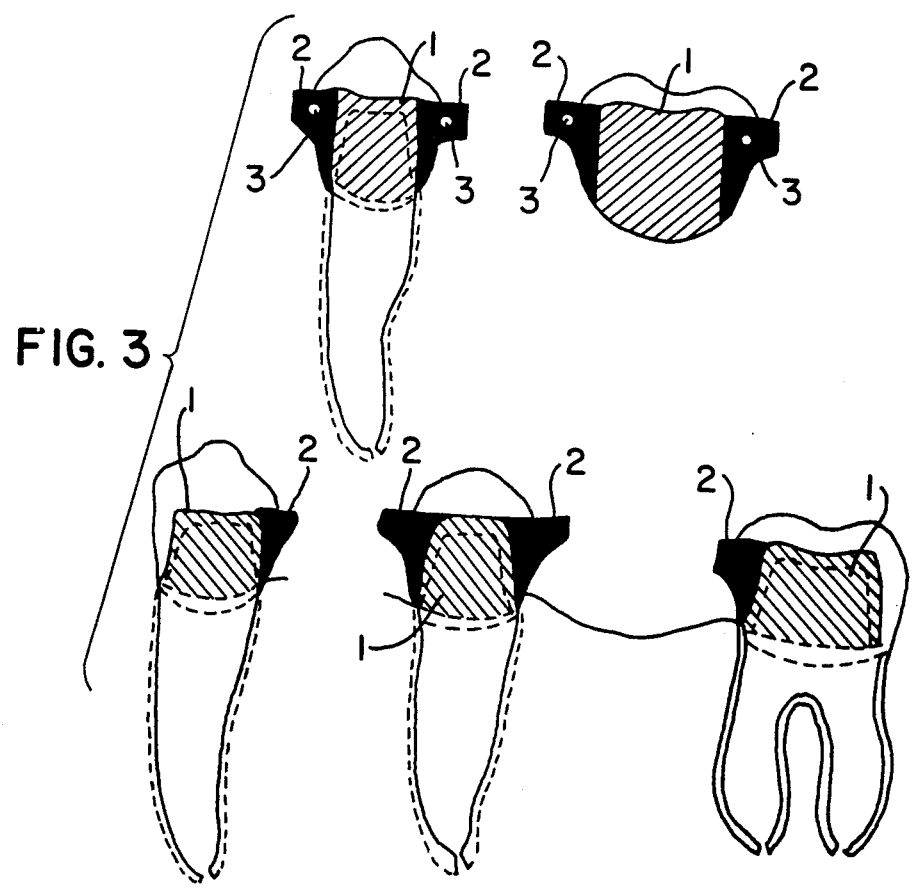
FIG. 3 is a side view of a plurality of individual crown elements according to the present invention with the prepared original teeth of the patient shown in phantom.
Figure 4:
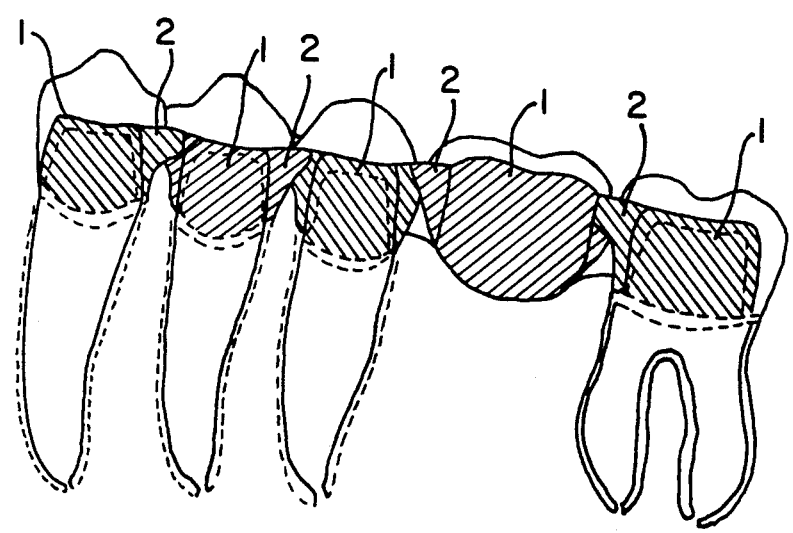
FIG. 4 is a side view of the elements of FIG. 3 welded together and forming a bridge.
Figure 7A:
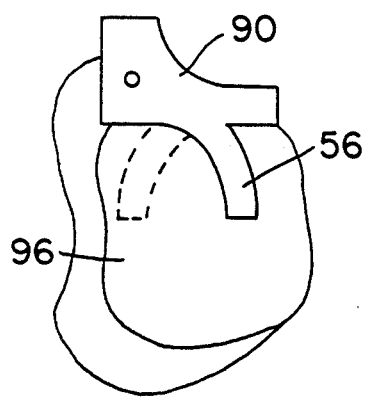
FIGS. 7A-7C are views similar to FIGS. 5A-5C showing alternative constructions of the coupling portion of the jointing means of the present invention.
Figure 7B:
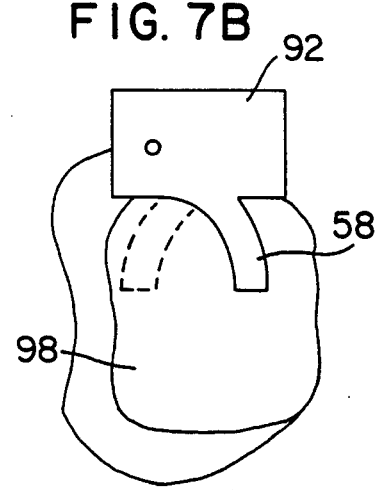
Figure 7C:
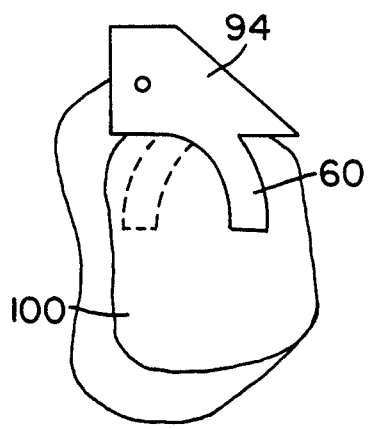
Figure 8A:
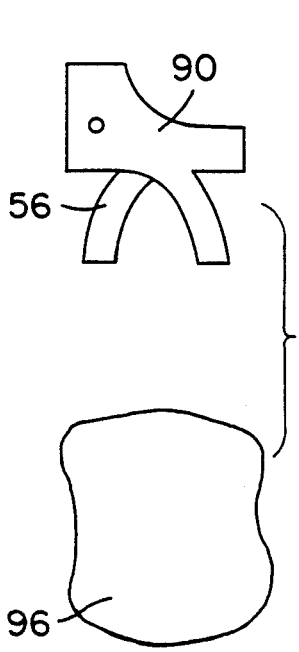
FIGS. 8A-8C are side views of the elements of FIGS. 7A-7C prior to attachment.
Figure 8B:
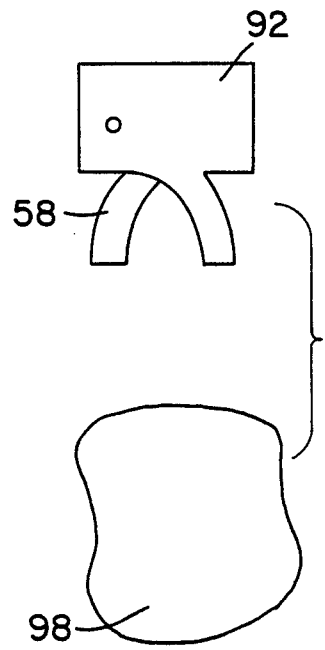
Figure 8C:
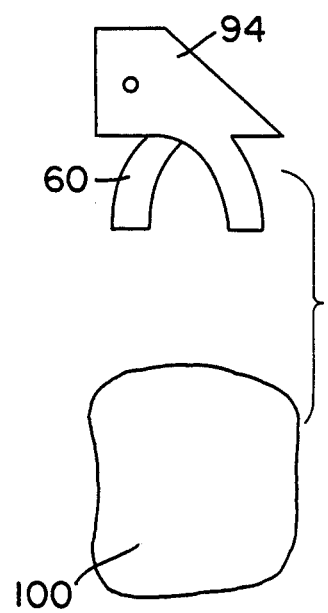
Figure 9A:
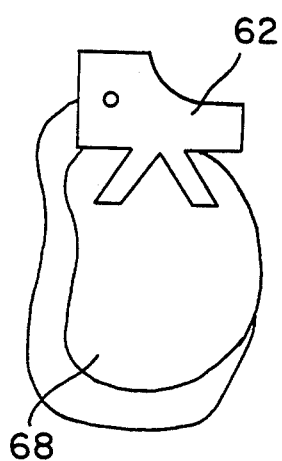
FIGS. 9A-9C are side views similar to FIGS. 5A-5C and showing an alternate construction of the coupling portion of the jointing means.
Figure 9B:
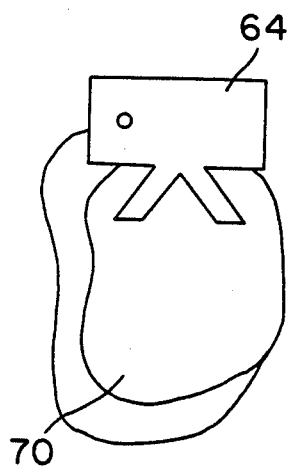
Figure 9C:
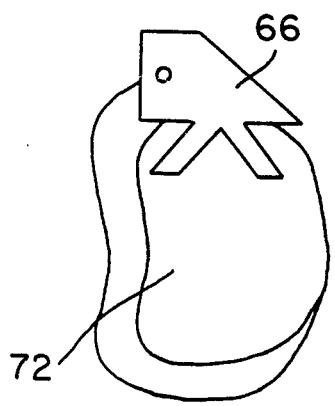
Figure 10A:
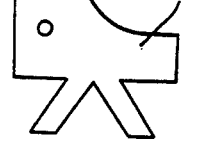
FIGS. 10A-10C are side views showing the jointing means of FIGS. 9A-9C prior to attachment.
Figure 10B:
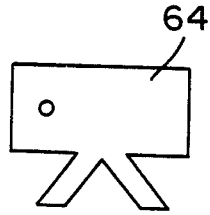
Figure 10C:
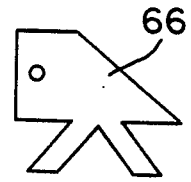

Referring now to the drawings, wherein like numerals indicate like parts, FIG. 1 illustrates crown elements constructed in accordance with the present invention. These crown elements include a tooth-shaped cap portion 1 which is provided on at least one of the sides with a jointing tab 2. As shown in FIG. 2, each jointing tab 2 is constructed to be welded to the corresponding tab extending from an adjacent crown. In this regard, two tabs extend from the middle replacement elements of the structure so that each side of a middle element can be welded to the adjacent crowns.

In order to facilitate welding, one or more microindentations 3 may also be included on the inside lateral surfaces of the jointing tabs 2, although welding could, of course, be carried out without the microindentations.

The dental structure shown in FIGS. 1-4 is preferably comprised of high purity titanium metal, although high concentration titanium alloys such as in the form of aluminum are suitable for resistance welding and may also be used. The use of titanium significantly reduces the cost of the dental material in cases in which gold would otherwise be used. Moreover, the weldability and the reweldability of the individual crown or bridge elements reduces the complications encountered with installation, repair, removal or modification. In this connection, in relatively extended restoration operations the removal of one or more individual replacement tooth elements is easier. It is sufficient to destroy an aesthetic portion, cut the structure, treat and modify the tooth replacement element, reweld with a suitable welding machine and to repair the aesthetic portion without the necessity of replacing or even removing the entire dental structure.

The possibility of working in the manner disclosed above is very significant in the event of a break in the aesthetic portion of one element or the weakening of a weld area or the loss of dental cement, as it is possible to remove and repair the damaged area individually and then reweld the repaired area.

Still further, the present invention allows for optimal positioning of the various elements because the welding operation is carried out after the dental cement has hardened so that drawbacks are eliminated which occur at the present time as regards parallelism problems, this being due to the fact that the divergent elements receive the dental cement separately and are then separately welded in the mouth.

In addition, besides making the various dental operations easier, the present invention reduces the drawbacks encountered in bridge work, such as gingival retraction, periaplical lesions, and the like. The present invention is advantageously employed also in the inplantation techniques, wherein an implantation can be definitely immobilized during the surgical procedure by fixing the same to the mesostructure which has already received the dental cement.

Still further, it has been observed that the use of titanium materials as described with reference to the present invention reduces the formation of plaque on the replacement tooth. In this regard, it is believed that the titanium may combine with other components in the mouth of the patient and form a surface incompatible with the growth of plaque.

Preferably, the titanium used in the present invention is a high purity metal or an alloy containing 80-99.9% titanium, in particular the alloys of the Grade 1–Grade 5 series (AESTM-B265/348/337). The mechanical characteristics of such titanium alloys are suitable for use in dentistry, as can be observed from the following table in which the values of some characteristics of said alloys are reported and, for a comparison, the values of the same characteristics of the gold alloys commonly employed in dentistry are reported.

|     |                                        | titanium alloy Grade 1 | gold | titanium alloy Grade 5 | gold |
|-----|----------------------------------------|------------------------|------|------------------------|------|
| (A) | hardness HB %                          | 140                    | 65   | 310                    | 188  |
| (B) | ultimate tensile stress, kg/mm$^2$     | 30–45                  | 61   | 90–100                 | 145  |
| (C) | elastic strength 0.2%, kg/mm$^2$       | 20                     | 20   | 85–89                  | 103  |
| (D) | elongation, %                          | 25–30                  | 22   | 8–10                   | 4    |

It is also to be considered that such characteristics are obtained with titanium alloy thicknesses much lower than those which are to be used in gold, so that the advantages of less filing work when treating the tooth and of a greater amount of white surface are obtained. For example, gold-platinum cast alloy crowns frequently must be at least 0.5 mm and preferably are 0.6 mm thick. Titanium crowns, however, generally need only be about 0.3 to 0.4 mm thick, depending on the specific form of titanium used.

As shown in FIGS. 5A, 5B and 5C thru 10A, 10B and 10C, the present invention additionally comprises weldable jointing implements or means which may form part of the titanium dental structures described above or which may be used in combination with gold crowns or with crowns made up of another noble metal or nonnoble dentally suitable metal. The laminate jointing means are preferably comprised of a high titanium concentration alloy or with another alloy that is capable of being welded in the mouth. Each of the jointing means is designed for coupling at one end to the tooth shaped cap portion of a crown element and provides a surface for a welded connection to the corresponding jointing means of an adjacent crown element.

When used in combination with gold or gold alloy, or another dentally suitable but non-weldable material, the jointing means of the present invention comprises at one end a shaped element to be rigidly coupled with the tooth-shaped cap portion such as by screwing, by the use of restrained or fixed joints, by overlapping, or by any other form of human mechanical fixing.

As mentioned previously, the welding surface of the jointing means may include one or more microindentations on the inside lateral surface to facilitate the welding operations, although such microindentations are not essential to the welding procedure. Also as noted above, use of laminate jointing means in accordance with the present invention advantageously avoids problems associated with parallelism, as the welding operation is carried out when the dental cement has already been put into place.

The jointing means is preferably constructed of high purity titanium metal or a high titanium concentrated alloy. In addition, the jointing means is of a thickness of from about 0.2 mm to about 4 mm, with a thickness of 0.8 mm being particularly preferred.

In the preferred embodiments according to the present invention, the shaped element of the jointing laminate is made up of a threaded body, which is advisable in the case of riding elements (dental bridges) and in the Richmond crowns, or the element may be dovetail shaped or a drop shape, or of the shape of a hollow portion of a cylinder, etc., provided that the corresponding cap portion is fashioned to receive the shaped element in a tight mechanical fit.

With particular reference to FIGS. 5A-5C and 6A-6C, a series of jointing means 32, 34 and 36, before and after their coupling with the corresponding crowns 38, 40 and 42, respectively, can be observed. The jointing means are each provided at one end with threaded element 44, 46, 48 which is designed for being coupled into the female threads 50, 52, 54 machined into the crown bodies. According to this arrangment, the female threads are obtained within the crowns by either overfusion of a preformed female part or threading, for instance by turning the element which has already been cast with the suitable internal diameter.

In FIGS. 7A-7C and 8A-8C, different couplings 56, 58 and 60 can be observed. Couplings 56, 58 and 60 have welding surfaces 90, 92 and 94 which are shown in attached and non-attached positions with crowns 96, 98 and 100. Attachment is achieved by overfusions between the jointing means 56, 58 and 60 and the crowns 96, 98 and 100, which have hollow portions for receiving the shaped elements.

Similarly, in FIGS. 9A-9C and 10A-10C, the shaped elements 62, 64 and 66 are joined with crowns 68, 70 and 72, also by overfusion.

Figure 11:
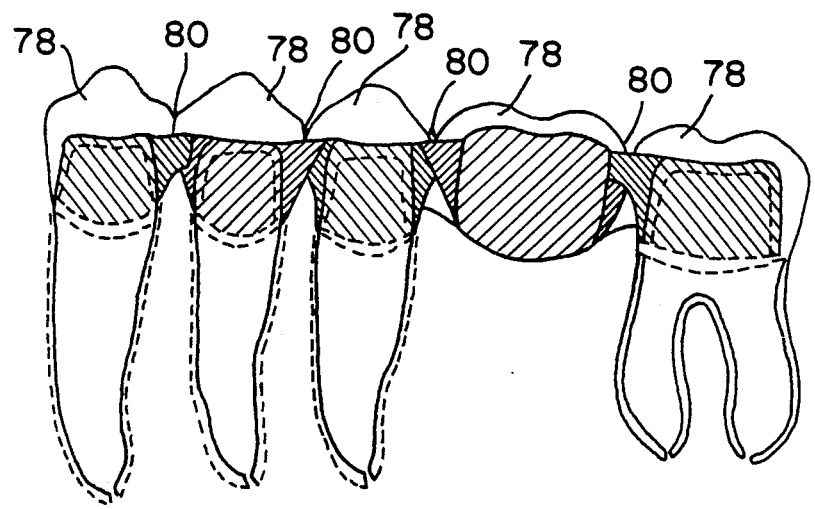
FIG. 11 is a side view of some of the elements of FIGS. 5-9 welded together in a patient's mouth.
Figure 12:
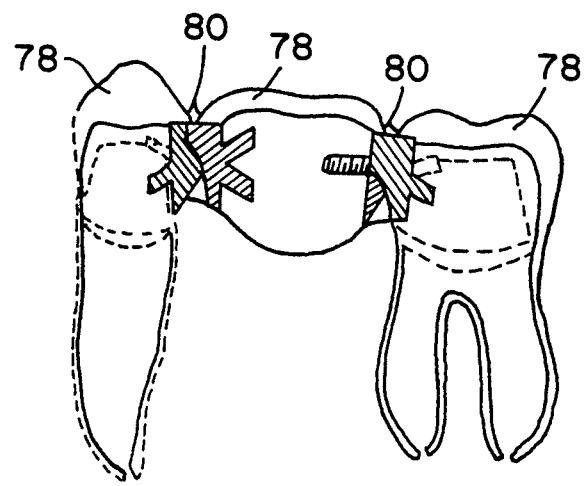
FIG. 12 is a side view similar to FIG. 10 but showing jointing means of different shapes welded together.

FIG. 11 depicts a series of crowns 78 which are coupled through the jointing means 80 of the present invention, which jointing means 80 are welded between themselves. In FIG. 12, the jointing means previously described are shown welded to dissimilarly shaped adjacent jointing means.

In describing the invention, reference has been made to preferred embodiments. However, those skilled in the art and familiar with the disclosure of the subject invention, may recognize additions, deletions, substitutions, modifications and/or other changes which will fall within the purview of the invention as defined in the following claims.

What is claimed is:

1. A dental crown comprising an outer aesthetic shell-like portion, a central cap portion contained within said outer aesthetic shell-like portion, and jointing means connected to a side of said central cap portion within said outer aesthetic shell-like portion, said jointing means extending through said outer aesthetic shell-like portion for providing a welding surface exterior of said aesthetic shell-like portion, said jointing means comprising at least one jointing tab formed from high purity titanium metal and having a generally flat configuration so that said welding surface provided exterior of said aesthetic shell-like portion comprises a generally flat welding surface which is capable of overlapping a generally flat welding surface provided by a jointing tab extending from at least one adjacent dental structure, whereby said dental crown is capable of being welded to said at least one adjacent dental structure.

2. A dental crown as recited in claim 1, wherein said jointing tab has a length running parallel to an imaginary line between said central cap portion and said at least one adjacent dental structure in the mouth of the patient, a height in a direction parallel to a vertical height of the dental crown, and a thickness in a direction perpendicular to both the length and the height, the length and the height each being greater than the thickness, whereby said jointing tab is generally flat in configuration.

3. A dental crown comprising an outer aesthetic shell-like portion, a central cap portion contained within said outer aesthetic shell-like portion, and jointing means connected to a side of said central cap portion within said outer aesthetic shell-like portion, said jointing means extending through said outer aesthetic shell-like portion for providing a welding surface exterior of said aesthetic shell-like portion, said jointing means comprising at least one jointing tab formed from highly concentrated titanium alloy containing about 80% to 99.9% titanium and having a generally flat configuration so that said welding surface provided exterior of said aestheric shell-like portion comprises a generally flat welding surface which is capable of overlapping a generally flat welding surface provided by a jointing tab extending from at least one adjacent dental structure, whereby said dental crown is capable of being welded to said at least one adjacent dental structure.

4. A dental crown as recited in claim 1 or 3, wherein said jointing tab has an inside surface on which at least one microindentation is provided, whereby welding of said jointing tab to said at least one adjacent dental structure is facilitated.

5. A dental bridge comprising a plurality of dental crowns as recited in any one of claims 1 or 3, wherein adjacent dental crowns are welded together.

6. A jointing implement for carrying out a welding operation with respect to a first dental structure and a second dental structure, said jointing implement comprising:

a surface comprising a lamina of high purity titanium by means of which said jointing implement is weldable to said first dental structure; and coupling means comprising a shaped element connected to said high purity titanium surface for mechanically coupling said high purity titanium surface to said second dental structure, said second dental structure containing a correspondingly shaped cavity for receiving said shaped element;

whereby said first dental structure and said second dental structure are weldably interconnected.

7. An implement as recited in claim 6, wherein said shaped element is dovetail-shaped and is insertable into a correspondingly shaped cavity in said second dental structure.

8. An implement as recited in claim 6, wherein said shaped element is drop-shaped and is insertable into a correspondingly shaped cavity in said second dental structure.

9. An implement as recited in claim 6 wherein said shaped element is a threaded connector.

10. A jointing implement for carrying out a welding operation with respect to a first dental structure and a second dental structure, said jointing implement comprising:

a surface comprising a lamina of high concentration titanium alloy containing about 80% to 99.9% titanium, by means of which said jointing implement is weldable to said first dental structure; and coupling means comprising a shaped element connected to said high concentration titanium alloy surface for mechanically coupling said high concentration titanium alloy surface to said second dental structure, said second dental structure containing a correspondingly shaped cavity for receiving said shaped element;

whereby said first dental structure and said second dental structure are weldably interconnected.

11. A jointing implement for attachment to a dental element so as to permit connection between said dental element and similar adjoining dental elements by welding in the mouth of a patient, said jointing implement comprising a lamina formed from an alloy containing about 80% to 99.9% titanium, and a shaped element connected to said lamina, wherein the thickness of said lamina is from 0.2 mm. to 4 mm., and wherein said lamina has an inside lateral surface and is provided with at least one projection on said inside lateral surface in order to facilitate a welding operation in the mouth of the patient, whereby said dental element is capable of being welded to said similar adjoining dental elements in the mouth of the patient.

* * * * *